(12) United States Patent
Alqanee

(10) Patent No.: US 8,680,697 B2
(45) Date of Patent: Mar. 25, 2014

(54) ROADWAY BUMP ELECTRICITY GENERATION SYSTEM

(71) Applicant: Jasem M. J. Alqanee, Alsalam (KW)

(72) Inventor: Jasem M. J. Alqanee, Alsalam (KW)

( * ) Notice: Subject to any disclaimer, the term of this patent is extended or adjusted under 35 U.S.C. 154(b) by 0 days.

(21) Appl. No.: 13/682,569

(22) Filed: Nov. 20, 2012

(65) Prior Publication Data

US 2013/0127176 A1    May 23, 2013

Related U.S. Application Data

(60) Provisional application No. 61/561,990, filed on Nov. 21, 2011.

(51) Int. Cl.
| | | |
|---|---|---|
| *F02B 63/04* | (2006.01) | |
| *H02K 7/10* | (2006.01) | |
| *H02K 7/18* | (2006.01) | |
| *F03G 7/08* | (2006.01) | |

(52) U.S. Cl.
USPC .......................................... 290/1 C; 290/1 R

(58) Field of Classification Search
USPC .................................................. 290/1 C, 1 R
See application file for complete search history.

(56) References Cited

U.S. PATENT DOCUMENTS

| | | | | |
|---|---|---|---|---|
| 2,020,361 A | * | 11/1935 | Johnston | 417/214 |
| 4,144,601 A | * | 3/1979 | Anderson et al. | 5/118 |
| 4,173,431 A | * | 11/1979 | Smith | 417/229 |
| 4,238,687 A | * | 12/1980 | Martinez | 290/1 R |
| 4,239,975 A | * | 12/1980 | Chiappetti | 290/1 R |
| 4,739,179 A | * | 4/1988 | Stites | 290/1 R |
| 4,980,572 A | * | 12/1990 | Sen | 290/1 R |
| 5,157,922 A | * | 10/1992 | Baruch | 60/325 |
| 5,355,674 A | * | 10/1994 | Rosenberg | 60/325 |
| 5,570,286 A | * | 10/1996 | Margolis et al. | 701/36 |
| 5,634,774 A | * | 6/1997 | Angel et al. | 417/229 |
| 6,091,159 A | * | 7/2000 | Galich | 290/1 R |
| 6,172,426 B1 | * | 1/2001 | Galich | 290/1 R |
| 6,204,568 B1 | * | 3/2001 | Runner | 290/1 R |
| 6,206,049 B1 | * | 3/2001 | Ward | 138/98 |
| 6,353,270 B1 | * | 3/2002 | Sen | 290/1 R |
| 6,376,925 B1 | * | 4/2002 | Galich | 290/1 R |
| 6,494,144 B1 | * | 12/2002 | Perez Sanchez | 104/287 |
| 6,734,575 B2 | * | 5/2004 | Ricketts | 290/1 R |
| 6,756,694 B2 | * | 6/2004 | Ricketts | 290/1 R |
| 6,767,161 B1 | * | 7/2004 | Calvo et al. | 404/71 |
| 6,858,952 B2 | * | 2/2005 | Gott et al. | 290/1 R |
| 6,936,932 B2 | * | 8/2005 | Kenney | 290/1 R |
| 6,949,840 B2 | * | 9/2005 | Ricketts | 290/1 R |
| 6,969,213 B2 | * | 11/2005 | Rastegar et al. | 404/11 |
| 7,067,932 B1 | * | 6/2006 | Ghassemi | 290/1 R |
| 7,145,257 B2 | * | 12/2006 | Ricketts | 290/1 R |
| 7,179,205 B2 | * | 2/2007 | Schmidt | 482/70 |
| 7,239,031 B2 | * | 7/2007 | Ricketts | 290/1 R |
| 7,419,326 B2 | * | 9/2008 | Rastegar et al. | 404/71 |

(Continued)

FOREIGN PATENT DOCUMENTS

| | | |
|---|---|---|
| DE | 41 42 492 A1 | 7/1992 |
| KR | 10-2004-0017559 | 2/2004 |

*Primary Examiner* — Pedro J Cuevas
(74) *Attorney, Agent, or Firm* — Richard C. Litman

(57) ABSTRACT

The roadway bump electricity generation system converts kinetic energy obtained from a vehicle into electrical energy, which is intended for use on roads, highways and parking garages. At least one guide-mounted, spring-loaded member is disposed in the roadway and operates an electric generator when displaced by the vehicle wheels rolling over the bump.

7 Claims, 9 Drawing Sheets

(56) References Cited

U.S. PATENT DOCUMENTS

| | | | |
|---|---|---|---|
| 7,530,760 B2 * | 5/2009 | Rastegar et al. | 404/10 |
| 7,530,761 B2 * | 5/2009 | Kenney | 404/71 |
| 7,541,684 B1 * | 6/2009 | Valentino | 290/1 R |
| 7,589,427 B2 * | 9/2009 | Davis | 290/1 R |
| 7,605,482 B2 * | 10/2009 | Brown et al. | 290/1 R |
| 7,626,279 B2 * | 12/2009 | Brown et al. | 290/1 R |
| 7,629,698 B2 * | 12/2009 | Horianopoulos et al. | 290/1 R |
| 8,123,431 B2 * | 2/2012 | Chen | 404/71 |
| 8,164,204 B2 * | 4/2012 | Jang | 290/1 R |
| 8,217,523 B2 * | 7/2012 | Brown et al. | 290/1 R |
| 8,251,183 B2 * | 8/2012 | Chen | 185/39 |
| 8,334,603 B2 * | 12/2012 | Daya | 290/1 R |
| 8,344,527 B2 * | 1/2013 | Becerra | 290/1 R |
| 8,497,589 B2 * | 7/2013 | Geletka | 290/1 R |
| 2002/0089309 A1 * | 7/2002 | Kenney | 322/1 |
| 2003/0116211 A1 * | 6/2003 | Ward | 138/98 |
| 2004/0160058 A1 * | 8/2004 | Gott et al. | 290/1 R |
| 2007/0111864 A1 * | 5/2007 | Schmidt | 482/70 |
| 2007/0126239 A1 * | 6/2007 | Stewart et al. | 290/53 |
| 2009/0197743 A1 * | 8/2009 | Schmidt | 482/52 |
| 2009/0315334 A1 * | 12/2009 | Chen | 290/1 A |
| 2010/0144496 A1 * | 6/2010 | Schmidt | 482/70 |
| 2011/0215589 A1 * | 9/2011 | Chen | 290/1 |
| 2013/0213744 A1 * | 8/2013 | Foley | 187/276 |

* cited by examiner

US 8,680,697 B2

ROADWAY BUMP ELECTRICITY GENERATION SYSTEM

CROSS-REFERENCE TO RELATED APPLICATION

This application claims the benefit of U.S. Provisional Patent Application Ser. No. 61/561,990, filed Nov. 20, 2011 and U.S. Provisional Patent Application Ser. No. 61/561,717, filed Nov. 18, 2011.

BACKGROUND OF THE INVENTION

1. Field of the Invention

The present invention relates to renewable energy, and particularly to a roadway bump electricity generation system that provides for electricity generation by vehicular movement over a speed bump.

2. Description of the Related Art

There are numerous publications describing apparatus that generate electricity from wheeled vehicles passing over a bump along a road. Many of these devices are spring-loaded and convert movement of the device caused by the weight of a passing vehicle into electricity.

Nevertheless there remain problems relating to the smooth movement of vehicles over such devices. Moreover, many such devices require too much space in that both the mechanical movement and the electricity generator are housed underground in a hole beneath the bump.

Thus, a roadway bump electricity generation system solving the aforementioned problems is desired.

SUMMARY OF THE INVENTION

The roadway bump electricity generation system converts potential (weight) and kinetic (speed) energy obtained from a vehicle into electrical energy, which is intended for use on roads, highways and parking garages. At least one guide-mounted, spring-loaded member is disposed in the roadway and operates a dynamo when displaced by the weight of a passing vehicle.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The roadway bump electricity generation system provides a system for generating electric power from the movement of vehicles passing over a bump. The bump may be in the road, a highway, or in underground parking facilities. As a vehicle passes over the bump, the bump is moved reciprocally down and up. A rod attached to the bump is connected to a lever at its distal end. The lever is connected to a gear assembly that translates the linear up-down motion into a rotational gear motion. Rotational movement in the gearbox is coupled to a generator to produce high electric power.

Figure 1:
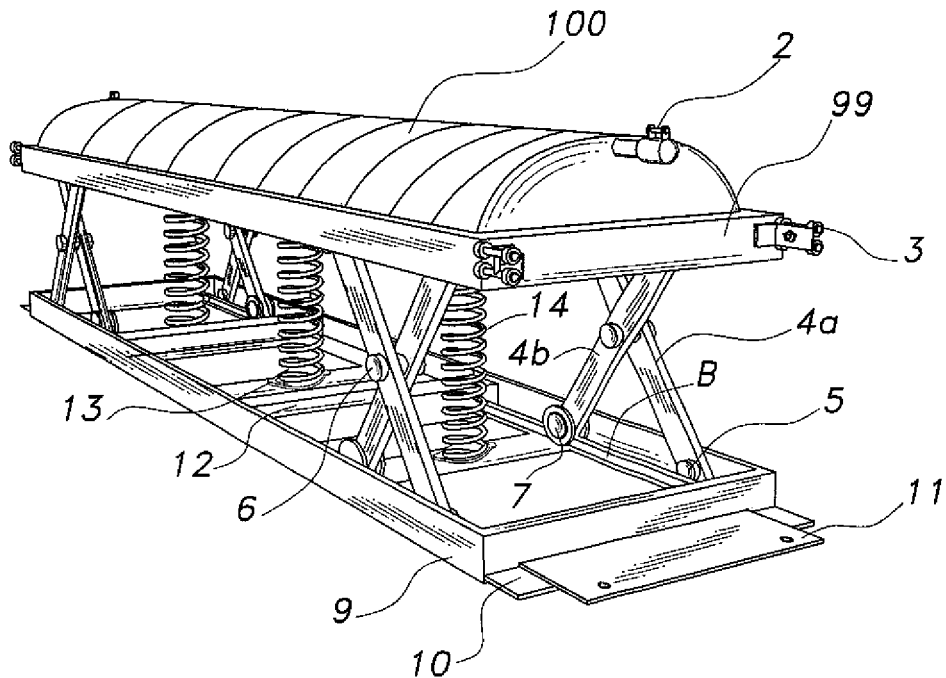
FIG. 1 is a perspective view of a bump portion of the roadway bump electricity generation system according to the present invention.
Figure 2:
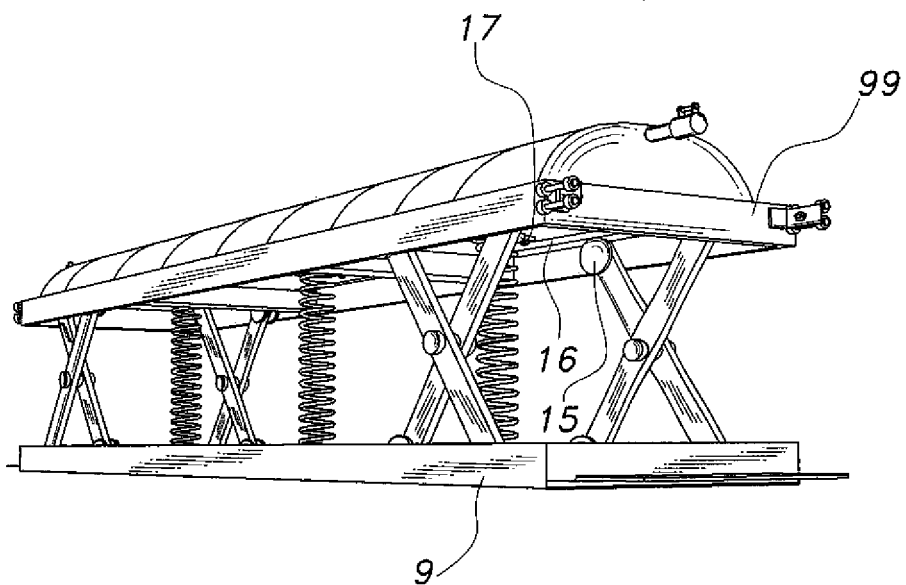
FIG. 2 is another perspective view of the bump portion of the roadway bump electricity generation system according to the present invention.
Figure 3:
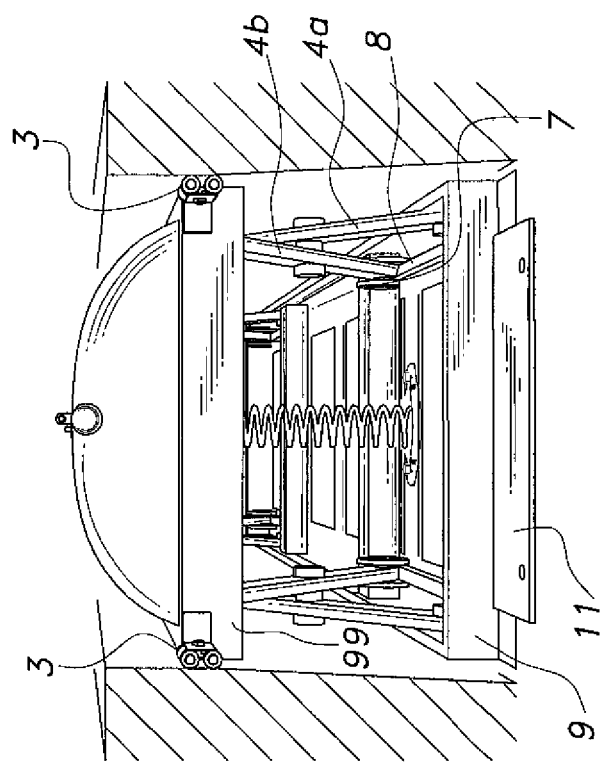
FIG. 3 is a front view of the bump portion of FIG. 1, shown in an extended position.
Figure 6:
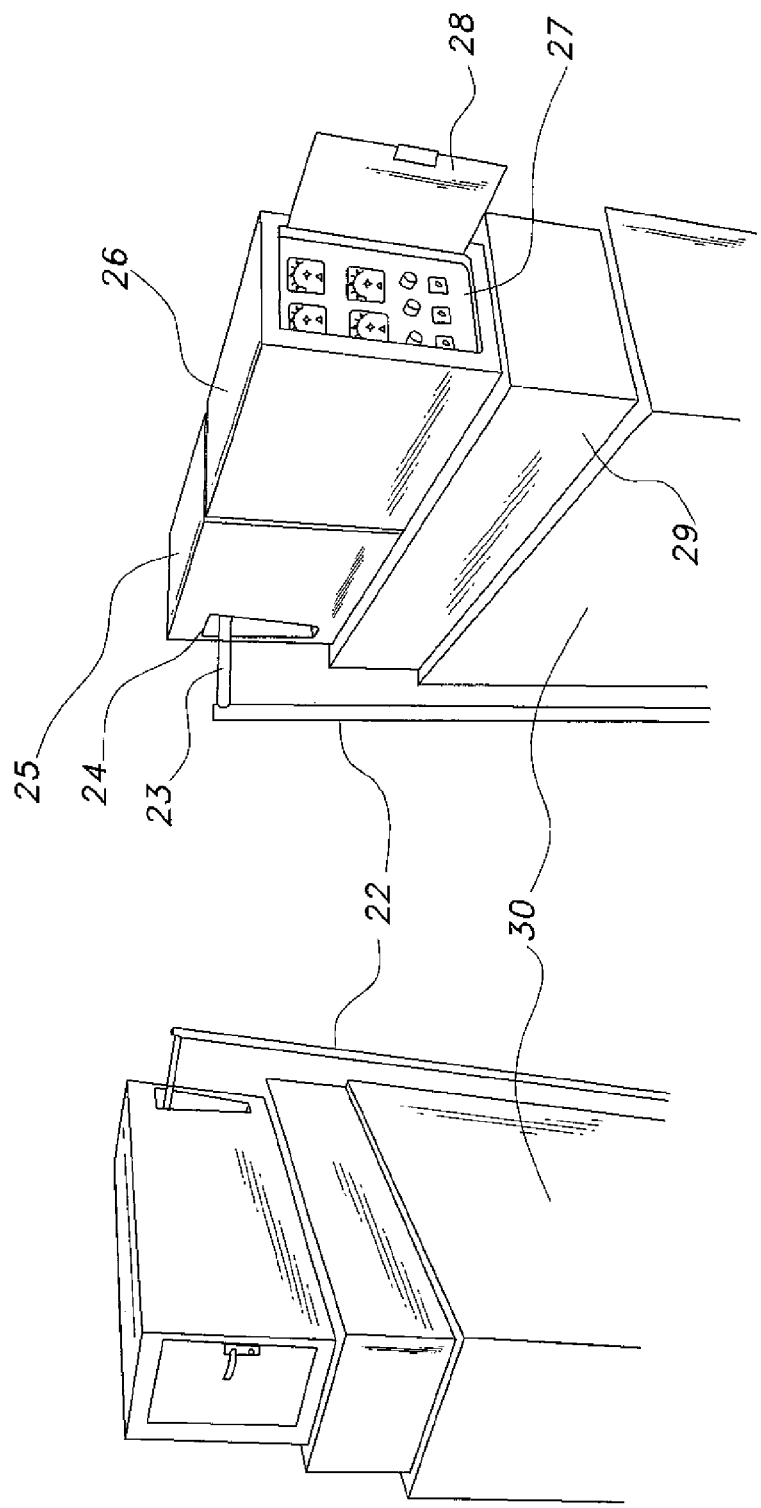
FIG. 6 is a partial perspective view showing the configuration of aboveground portions of the roadway bump electricity generation system according to the present invention as they would appear on opposite sides of a roadway.

As shown in FIG. 1, the device includes a metal cover 100 that is designed to be of similar dimension and height as the familiar concrete speed bump in the road. The metal cover 100 has an arm coupler 2 at each longitudinal end that provides an attachment point for a force driving rod 22 attached to the coupler 2, as shown in FIG. 6. The bump cover 100 is attached to an elongate upper frame 99 and maintains a normally raised position over an elongate lower frame 9 via compression support (as shown in FIG. 3) from below provided by springs 14, which are anchored at attachment points 13 to the lower frame 9, and also attached at upper frame attachment point 17 to the upper frame 99, as shown in FIGS. 1 and 2. Extending from the lower frame 9 is a side flange mount assembly 10 having an attachment plate 11 with mounting holes through which bolts can be disposed and threaded into an underground concrete structure to secure the unit in place.

Elongate scissor arms 4a and 4b are pivotally attached to each other at their midpoint, thereby facilitating scissor like relative pivotal movement. A plurality of assemblies of such scissor arms 4a and 4b is attached at each frame corner. One end of each of the scissor arms 4a and 4b is pivotally attached to the lower base 9 and to the upper base 99 at the frame corners. The opposite end of each scissor arms 4a and 4b have attached roller wheels 7 and 15 that roll in or on tracks defined by the rails 8 and 16 of the lower and upper frame 9, 99, respectively, as shown in FIGS. 1 and 2.

These wheels 7 and 15 permit the scissors arms assemblies 4a and 4b to freely slide over the rails 8 and 16. The lower frame 9 is disposed underground to support and attach all components of the speed bump unit. Balance attachment wheeled guides 3 add support to opening sidewalls in which the unit is disposed. These wheeled support guides 3 hug sidewalls of the pit 21 to give the bump more stability and ease of movement, while also constraining motion to upward and downward directions.

The weight of a vehicle passing over the bump is transmitted to the bump via the vehicle's wheels and causes the scissor arms 4b and 4a to extend while sliding horizontally along tracks in the rails 8 and 16 with the aid of lower and upper wheels 7 and 15 as the bump is pushed downward by the vehicle wheels.

Figure 4:
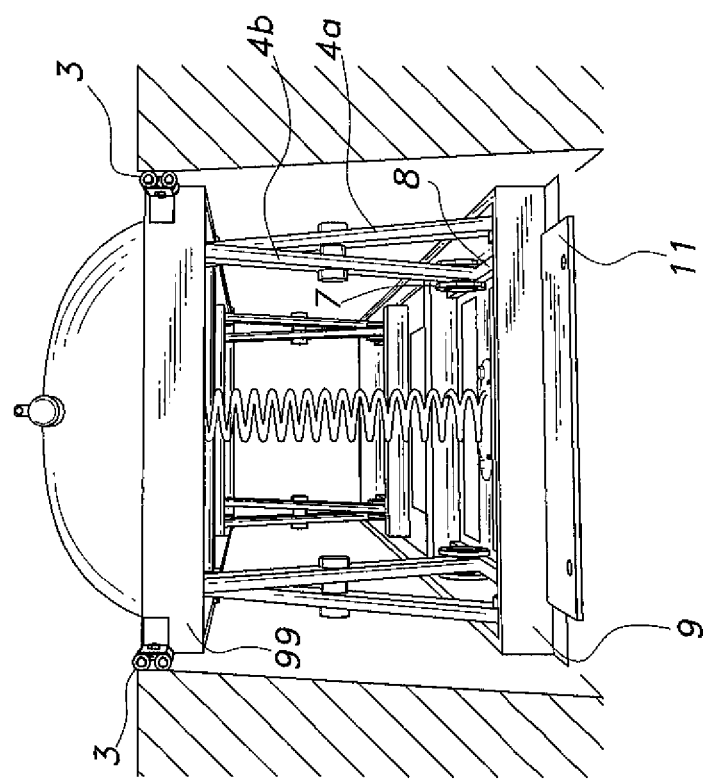
FIG. 4 is a front view of the bump portion of FIG. 1, shown in a compressed position.

As shown in FIG. 4, when the bump 100 is pushed down by the vehicle weight, the springs 14 are compressed. The movable arm pairs 4a and 4b extend along the tracks in rails 8, and 16 until they reach at least one stop member 12 disposed across the tracks in at least one of the upper or lower frames. The stop member 12 gives the bump more support to overcome the weight of any vehicle. The stop rod 12 limits downward movement of the bump and is positioned to stop movement of the bump when it has been displaced to a position horizontal with the ground surface. Also, when the bump moves downward, the attached arm coupler 2 is also moved downward, thereby pulling the force driving rod 22 downward, as shown in FIG. 6.

The force driving rod 22, which is attached to arm coupler 2, is pivotally linked to a gearbox crank arm 23, which therefore also pivots downward to turn gears in a gearbox 25 responsive to the downward motion of the bump. As the crank arm 23 reciprocates, a gear train in the gearbox 25 rotates a shaft (such as an armature shaft or rotor of a generator), which is connected to or part of an electric generator 26, so that the generator 26 rotates according to the specified transmission ratio of the gear train in the gearbox 25. Crank arms and gear trains that produce rotation of a shaft are well known, and need not be described further. The generator 26 produces electric power according to the rotation speed of the gears in the gearbox 25, and according to transformer or armature winding turns.

The gear train in the gearbox 25 has a plurality of gear stages used to produce high-speed rotation of the gear-driven generator 26. Thus, the generator 26 will rotate at a high speed to produce high electrical power. The generator will reach a speed of approximately 120 RPM, and the output electric power at 48V DC is more than 500 W. When the first tire of a vehicle, such as exemplary vehicle V, moves away from the bump, due to recoil action of the compressed springs 14, the bump will return to its normal extended position. During the returning process the force driving rod 22 is pushed up and again causes rotation of gears in the gearbox 25 on this upward return stroke. Thus, in all conditions the force driving rod 22 both reciprocates and rotates or vibrates right and left and causes gear train in the gearbox 25 to rotate the rotor of generator 26. A slot 24 in the gearbox housing is provided to allow the linked arms 22 and 23 to freely pivot in a drive plane of the assembly.

Measuring instrumentation 27 is disposed or displayed on a control panel in the front portion of an enclosure housing the generator 26 and is provided to indicate the measured value of voltage or current or power of the electric power from the generator 26. Also, for more security, the generator enclosure has a door 28 to seal the generator 26 from the elements, yet provides access for maintenance of the device.

The electric power output from the generator is used to charge a battery bank 29. The battery bank 29 has a plurality of batteries. The gearbox 25, the generator 26, and the storage battery bank 29 are disposed inside or atop a concrete pillar 30. FIG. 6 shows a first power generator assembly disposed on the left side of a roadway and a second unit disposed on the right side of the roadway.

In another embodiment of the system, the gearbox, the generator, and the batteries box may be disposed underground inside of a basement or pit beside the road or the highway, according to the design of the road or highway. Moreover, the gearbox, generator and the batteries box may be housed in a basement sidewall or beneath the sidewalls.

Figure 5:
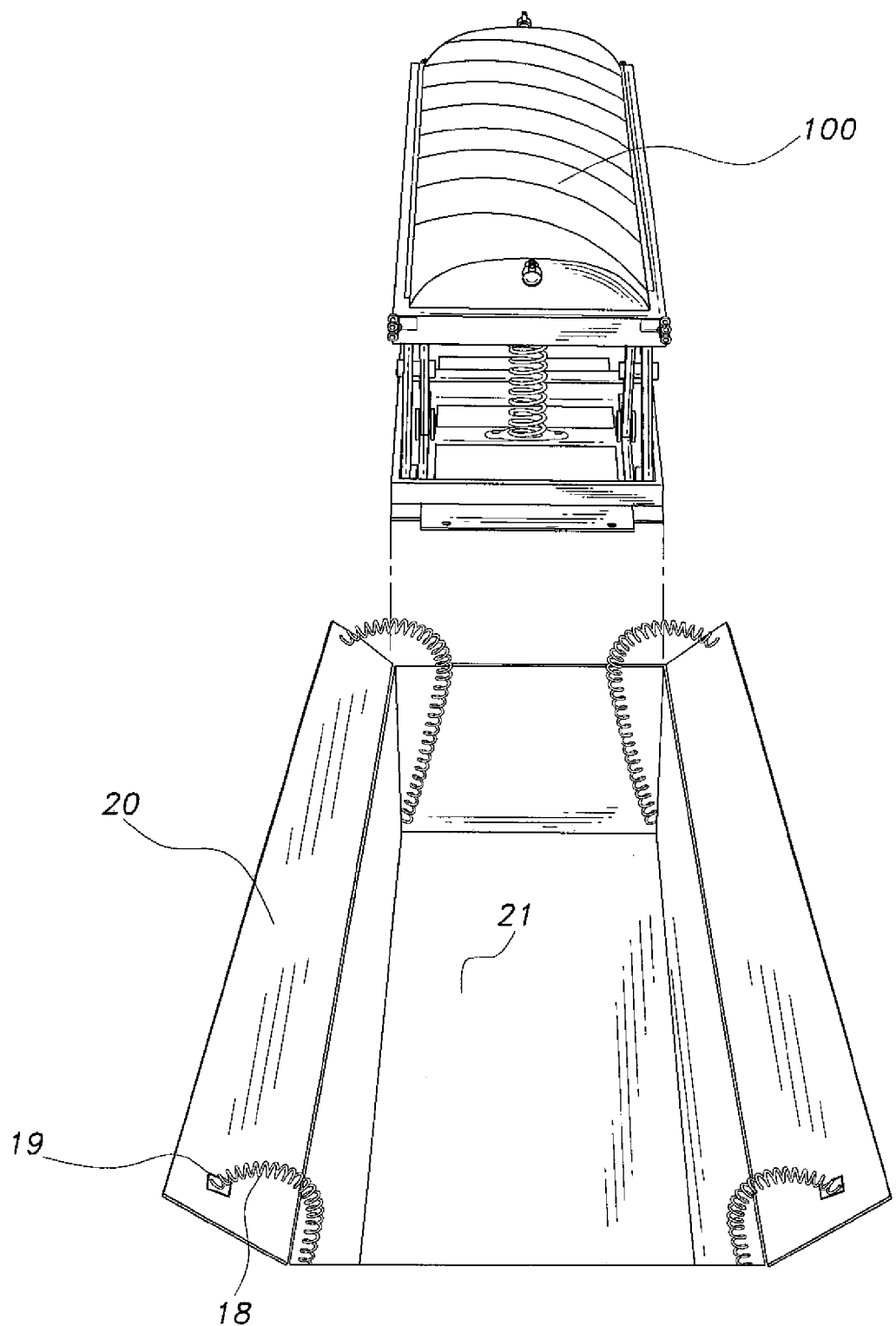
FIG. 5 is a perspective view of the roadway bump electricity generation system according to the present invention, showing the bump portion exploded from the receiving pit.

As shown in FIG. 5, the bump assembly is housed in a pit 21, which is covered with inclined flaps 20. The flaps are pivotally attached along longitudinal edges of the pit 21 by flexible springs 18. The springs 18 are secured to each flap 20 by a locking retainer 19. The springs 18 provide flexible movement of the flaps 20. The top side of the flaps 20 is lined black and white in order to be similar to a normal concrete speed bump.

Figure 7:
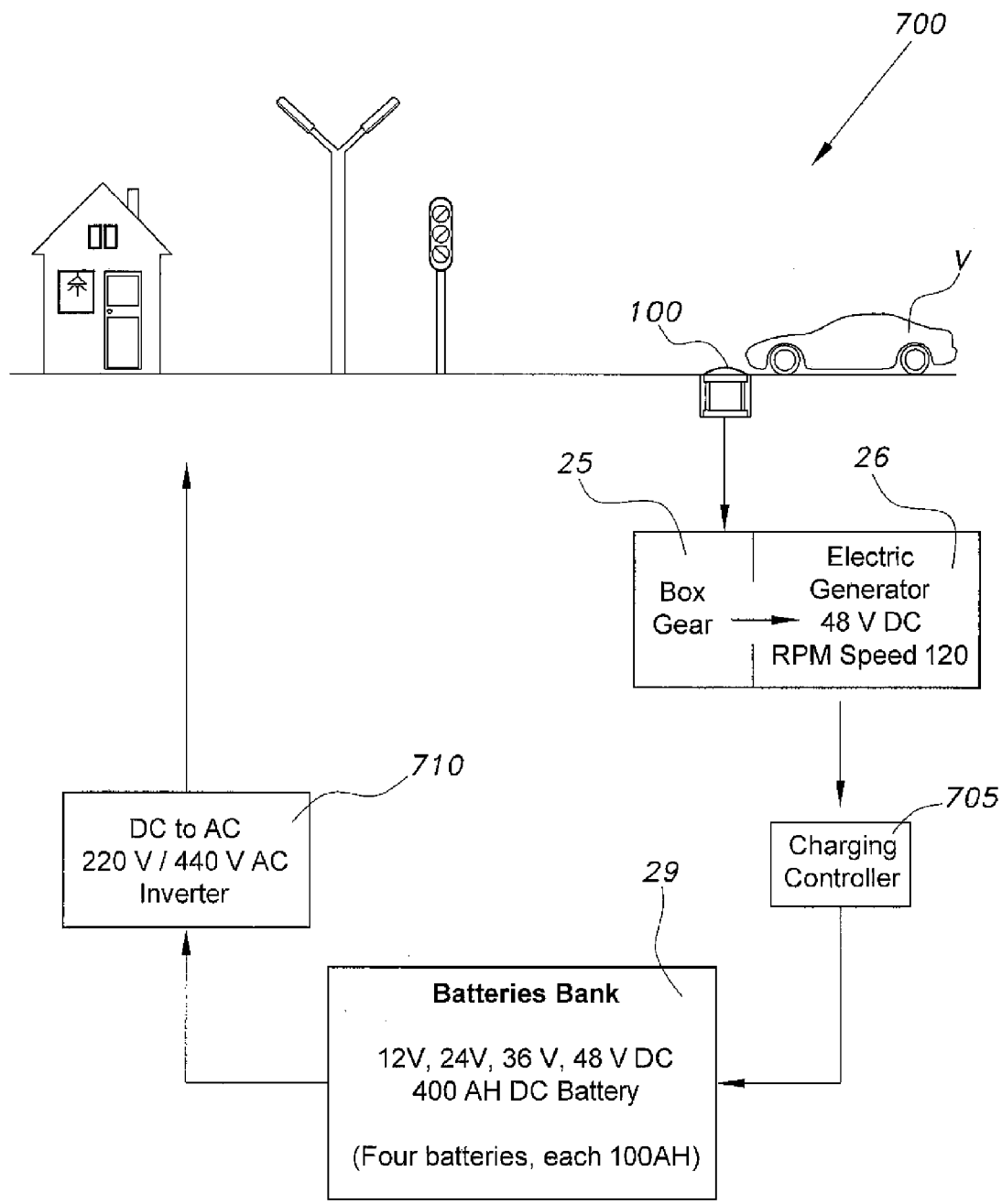
FIG. 7 is a block diagram describing electric power generation in the roadway bump electricity generation system according to the present invention.
Figure 8:
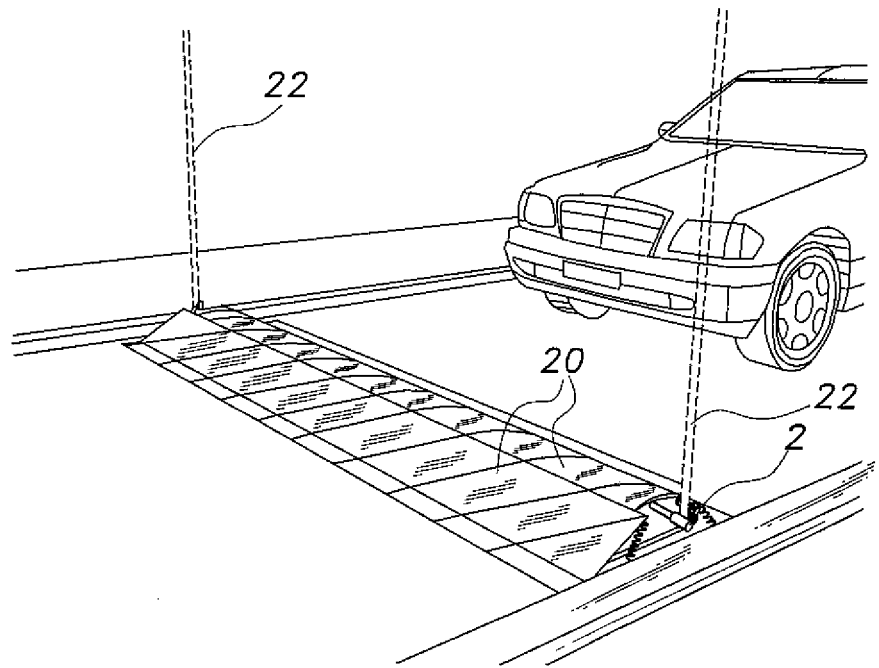
FIG. 8 is an environmental perspective view of an oncoming car about to actuate the roadway bump electricity generation system according to the present invention.
Figure 9:
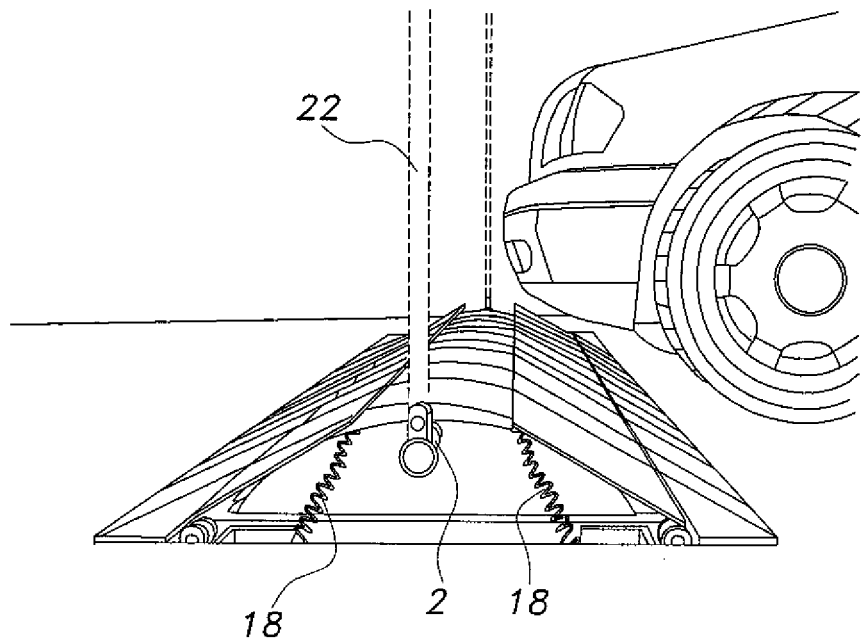
FIG. 9 is another environmental perspective view showing the oncoming car of FIG. 8 in relation to a bump of the roadway bump electricity generation system according to the present invention.
Figure 10:
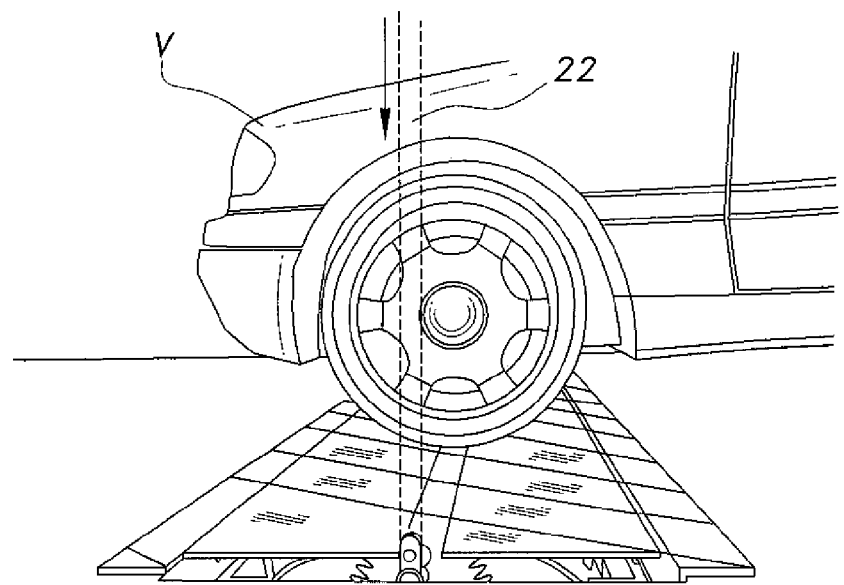
FIG. 10 is an environmental side view showing the roadway bump being displaced downward when the front tire of the vehicle passes over in the roadway bump electricity generation system according to the present invention.
Figure 11:
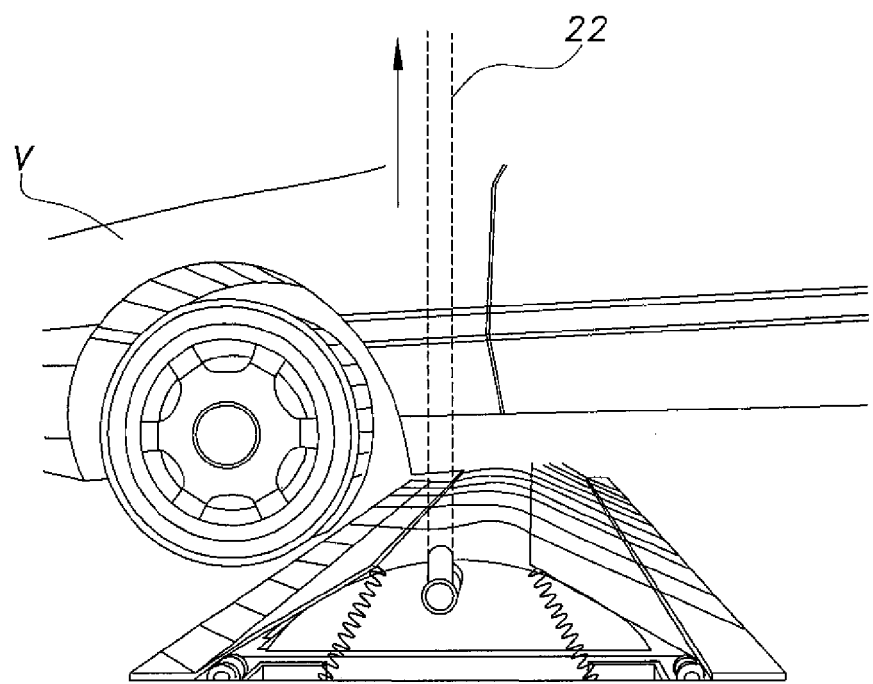
FIG. 11 is an environmental side view showing the roadway bump returning to its extended position after the vehicle has passed over a bump in the roadway bump electricity generation system according to the present invention.
Figure 12:
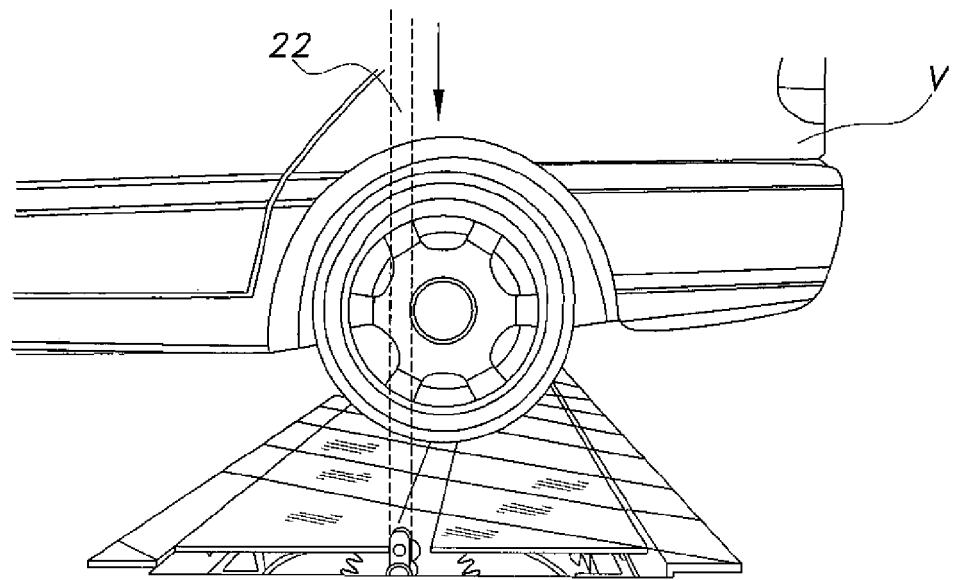
FIG. 12 is an environmental side view showing the roadway bump being displaced downward when the rear tire of the vehicle passes over a bump in the roadway bump electricity generation system according to the present invention.
Figure 13:
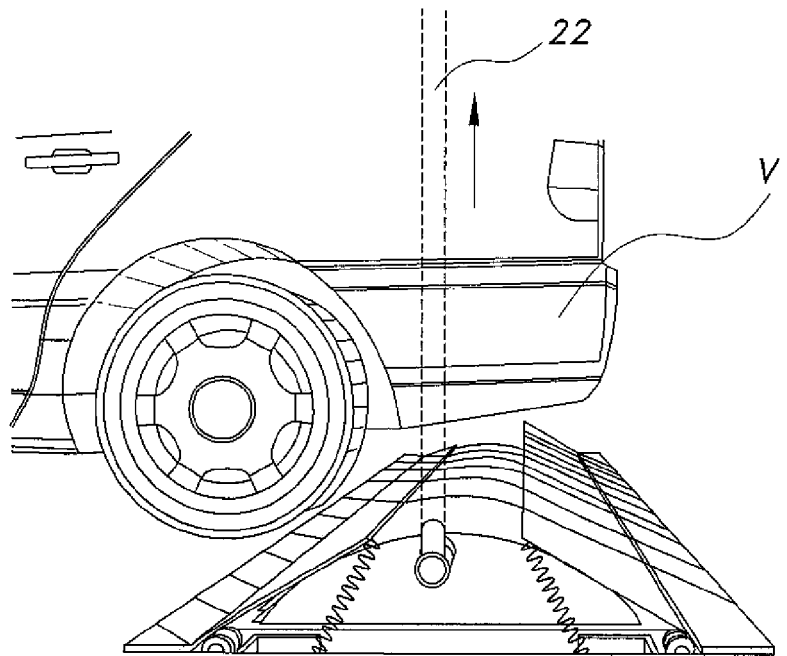
FIG. 13 is an environmental side view showing the roadway bump returning to its extended position after the rear tire of the vehicle has passed over a bump in the roadway bump electricity generation system according to the present invention.

As shown in the diagram 700 of FIG. 7, the output electric power of the generator is about 48V DC and 500 watts. The RPM of the generator, however, is not constant because it varies according to the weight, speed, and rate of vehicles passing over the bump. Therefore, a charging controller 705 is provided to regulate the charging rate of the battery bank 29. The charging controller 705 is connected between the generator 26 and the battery bank 29, and adjusts and controls the output power of the generator 26 to a constant value for charging the batteries 29. The battery bank 29 can be connected with a suitable destination (load) or used with a DC/AC inverter 710 to convert the DC values to AC 240 volts single phase and 440 volts three phase for electrical connection to a suitable destination. The battery bank 29 may comprise any combination of 12-, 24-, 36-, and 48-volt DC batteries, preferably each of 400 amp hour (AH) rating.

Figure 14:
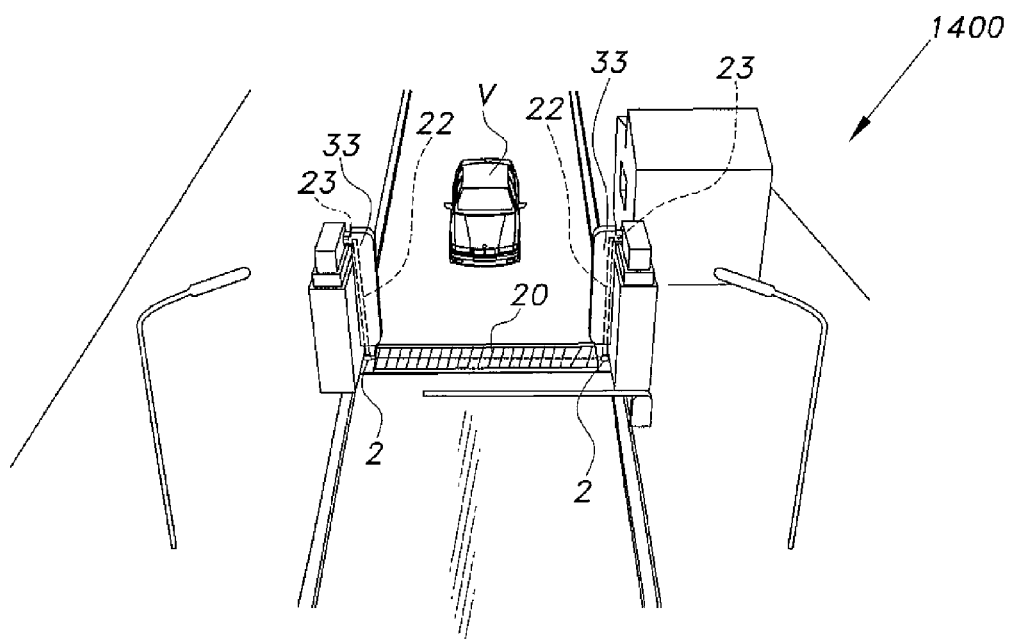
FIG. 14 is a perspective view of the roadway bump electricity generation system according to the present invention installed in a parking facility.
Figure 15:
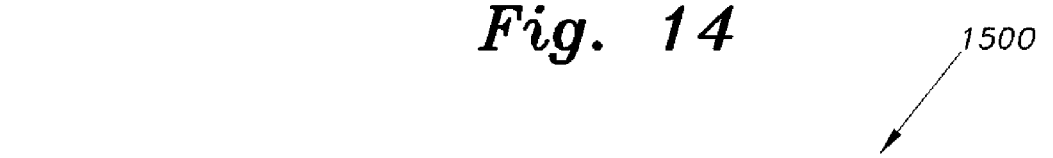
FIG. 15 is a perspective view of the roadway bump electricity generation system of FIG. 14 as seen from the rear.

FIGS. 8 through 13 illustrate positioning and movement of the bump assembly and force driving member 22 as a vehicle V passes with first front wheels in contact with the bump assembly, and then the rear wheels in contact with the bump apparatus. As shown in the parking garage installations 1400 and 1500 of FIGS. 14 and 15, the vertical driving rod 22 is housed inside vertically extending driving member enclosure 33, so it isn't visible to the vehicle occupants. The driving rod housing 33 may be, for example, a pipe 33. The diameter of the pipe 33 is larger than the diameter of the force driving member 22 to allow unimpeded power stroke motion of the force driving rod 22 inside the pipe housing 33.

It is to be understood that the present invention is not limited to the embodiments described above, but encompasses any and all embodiments within the scope of the following claims.

I claim:

1. A roadway bump electricity generation system, comprising:
   upper and lower elongated rectangular frame members, each of the frame members having elongated side rails defining tracks, each of the frame rails having a plurality of cross-members extending between the side rails, each of the frame members defining four corners;
   an arcuate bump member disposed atop the upper frame member;

a plurality of springs extending between the cross-members of the upper and lower frame members, the springs biasing the bump member upward;

a plurality of scissor assemblies extending between the upper and lower frames, each of the scissor assemblies having a pair of elongate arms pivotally attached substantially midway between their ends, each of the pairs having a first arm having a first end pivotally to one of the corners of the upper frame and a second arm pivotally attached to the corresponding corner of the lower frame, the first arm having a second end having a roller wheel attached thereto disposed in the track defined by the lower frame member, the second arm having a second end having a roller wheel attached thereto disposed in the track defined by the upper frame, each of the four corners having one of the scissor assemblies attached thereto;

means for constraining the bump contact member and the frame members to vertical displacement when the upper and lower frame members are disposed in a receiving pit below grade level;

a plurality of stop members disposed across the tracks of at least one of the frame members limiting travel of the roller wheels of each of the scissor assemblies configured so that a top portion of the bump member does not recede below grade level;

a pair of elongate force driving members, one of the force driving members being attached to each end of the bump member, respectively;

a pair of gearboxes disposed at opposite ends of the bump member, respectively;

a crank arm connecting each of the force driving members to a corresponding one of the gearboxes, respectively;

a pair of electric generators, each of the gearboxes having one of the generators linked thereto;

wherein, vehicles driving over the bump member cause resilient reciprocating movement of the bump member and the force driving members attached thereto, the crank arms translating reciprocating movement of the force driving members into rotational movement to drive the gearboxes and the generators to produce electricity.

2. The roadway bump electricity generation system according to claim 1, further comprising a charging controller connected to said electric generators, said charging controller adjusting and controlling output power of said electric generators to a constant value.

3. The roadway bump electricity generation system according to claim 2, further comprising storage batteries connected to said generators to store the electric power produced by said generators.

4. The roadway bump electricity generation system according to claim 3, further comprising a DC/AC inverter connected to said storage batteries, said inverter providing AC power for connection to an AC electrical power load.

5. The roadway bump electricity generation system according to claim 1, further comprising:

a receiving pit, said frames and said bump member being disposed in the receiving pit with the bump member extending above the pit, the pit having a forward edge and a rear edge;

front and rear bump member covering flaps pivotally attached to the front and rear edges of the pit, the flaps being adapted for covering front and rear portions of said bump member, respectively; and a plurality of springs connected between the pit and the front and rear flaps, the springs biasing the flaps to a position covering front and rear portions of said bump member.

6. The roadway bump electricity generation system according to claim 5, further comprising first and second aboveground housings disposed at opposite ends of said receiving pit, said gearboxes and said electric generators being disposed therein.

7. The roadway bump electricity generation system according to claim 6, further comprising:

a control panel disposed on said electric generators for displaying voltage, current, and power measurements and for mounting controls for adjusting generator output; and an access door disposed over each of the control panels.

* * * * *